US008258124B2

(12) United States Patent  
Weimar et al.

(10) Patent No.: US 8,258,124 B2
(45) Date of Patent: *Sep. 4, 2012

(54) COMBINATION MEDICAMENT

(75) Inventors: Christian Weimar, Constance (DE); Klaus Dietzel, Constance (DE); Helgert Müller, Radolfzell (DE); Degenhard Marx, Moos (DE)

(73) Assignee: Nycomed GmbH, Konstanz (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/973,350

(22) Filed: Dec. 20, 2010

(65) Prior Publication Data

US 2011/0086827 A1 Apr. 14, 2011

Related U.S. Application Data

(63) Continuation of application No. 10/537,356, filed as application No. PCT/EP03/14045 on Dec. 11, 2003, now Pat. No. 7,879,833.

(30) Foreign Application Priority Data

Dec. 12, 2002 (EP) .................................... 02027797
Feb. 13, 2003 (DE) ................................. 103 06 213

(51) Int. Cl.
*A01N 45/00* (2006.01)
*A61K 31/56* (2006.01)
*A61K 31/58* (2006.01)
*C07J 71/00* (2006.01)
*C07J 5/00* (2006.01)
*C07J 7/00* (2006.01)

(52) U.S. Cl. ............ 514/171; 514/174; 540/63; 540/70; 552/564; 552/566

(58) Field of Classification Search .................. 514/171, 514/174; 540/63, 70; 552/564, 566
See application file for complete search history.

(56) References Cited

U.S. PATENT DOCUMENTS

| 4,342,603 | A | 8/1982 | Daniels |
| 4,816,445 | A | 3/1989 | Mitsuhashi et al. |
| 5,112,407 | A | 5/1992 | Sakai et al. |
| 5,133,974 | A | 7/1992 | Paradissis et al. |
| 5,178,866 | A | 1/1993 | Wright et al. |
| 5,263,475 | A | 11/1993 | Altermatt et al. |
| 5,434,304 | A | 7/1995 | Trofast et al. |
| 5,474,759 | A | 12/1995 | Fassberg et al. |
| 5,482,934 | A | 1/1996 | Calatayud et al. |
| 5,733,901 | A | 3/1998 | Gutterer |
| 5,795,564 | A | 8/1998 | Aberg et al. |
| 5,811,388 | A | 9/1998 | Friend et al. |
| 5,840,917 | A | 11/1998 | Oi et al. |
| 6,030,604 | A | 2/2000 | Trofast |
| 6,068,833 | A | 5/2000 | Aberg et al. |
| 6,120,752 | A | 9/2000 | Oliver et al. |
| 6,124,268 | A | 9/2000 | Ghosal |
| 6,136,839 | A | 10/2000 | Isakson et al. |
| 6,241,969 | B1 | 6/2001 | Saidi et al. |
| 6,264,935 | B1 | 7/2001 | Chastaing et al. |
| 6,380,222 | B2 | 4/2002 | Lindberg et al. |
| 6,432,963 | B1 | 8/2002 | Hisamichi et al. |
| 6,475,467 | B1 | 11/2002 | Keller et al. |
| 6,528,527 | B2 | 3/2003 | Chang |
| 6,536,427 | B2 | 3/2003 | Davies et al. |
| 6,585,958 | B1 | 7/2003 | Keller et al. |
| 6,613,795 | B2 | 9/2003 | Noe et al. |
| 6,645,466 | B1 | 11/2003 | Keller et al. |
| 6,767,901 | B1 | 7/2004 | Nagano et al. |
| 6,866,839 | B2 | 3/2005 | Aberg et al. |
| 2002/0030068 | A1 | 3/2002 | Burt |
| 2002/0053344 | A1 | 5/2002 | Davies et al. |
| 2002/0065256 | A1 | 5/2002 | Karlsson et al. |
| 2002/0077346 | A1 | 6/2002 | Santus et al. |
| 2002/0111495 | A1* | 8/2002 | Magee et al. ................. 546/291 |
| 2002/0183292 | A1 | 12/2002 | Pairet et al. |
| 2003/0008019 | A1 | 1/2003 | Nishibe et al. |
| 2004/0050960 | A1 | 3/2004 | Godfrey et al. |
| 2004/0231666 | A1 | 11/2004 | Barker et al. |
| 2004/0247628 | A1 | 12/2004 | Lintz et al. |
| 2004/0266869 | A1 | 12/2004 | Montague et al. |
| 2005/0020637 | A1 | 1/2005 | Simon |
| 2005/0175546 | A1 | 8/2005 | Sambuco et al. |
| 2005/0245493 | A1 | 11/2005 | Marx et al. |
| 2006/0166953 | A1 | 7/2006 | Nishibe et al. |
| 2007/0025923 | A1 | 2/2007 | Wurst et al. |

FOREIGN PATENT DOCUMENTS

| DE | 41 29 535 A1 | 3/1992 |
| DE | 195 41 689 A1 | 5/1996 |
| EP | 0 407 028 B1 | 1/1991 |
| EP | 0 416 950 B1 | 3/1991 |
| EP | 0 416 951 B1 | 3/1991 |
| EP | 0 502 092 A1 | 9/1992 |
| EP | 0 505 321 A2 | 9/1992 |
| EP | 0 650 410 B1 | 5/1995 |
| EP | 0 691 865 B1 | 1/1996 |
| EP | 0 725 725 B1 | 8/1996 |

(Continued)

OTHER PUBLICATIONS

Vippagunta et al. Advanced Drug Delivery Reviews, 2001, vol. 48, pp. 3-26.*
Autoclave standard operating procedures, 2002, pp. 1-4.
Gennaro, Remington Farmacia, Tomo 2, 19th edition, vol. 2, Ed Medica Panamericana, p. 2249, 2005.
Material Safety Data Sheet for HPMC 2019 by Shin-Etsu Co, 2007.
Difluprednate; http://en.wikipedia.org/wiki/Difluprednate; printed Nov. 23, 2009.
Dent, "Ciclesonide", Current Opinion in Investigational Drugs, vol. 3, No. 1, pp. 78-83, (2002).
Schmidt, et al., "The New Topical Steroid Ciclesonide Is Effective in the Treatment of Allergic Rhinitis", J Clin Pharmacol, vol. 39, pp. 1062-1069, (1999).

(Continued)

*Primary Examiner* — Samira Jean-Louis
(74) *Attorney, Agent, or Firm* — Nath, Goldberg & Meyer; Sheldon M. McGee

(57) ABSTRACT

The subject matter of this application relates to the combination of ciclesonide or an epimer thereof with R,R-formoterol or a salt, or a hydrate of a salt thereof.

19 Claims, No Drawings

FOREIGN PATENT DOCUMENTS

| | | | |
|---|---|---|---|
| GB | 2 247 680 | A | 3/1992 |
| JP | 2001-48807 | A | 2/2001 |
| WO | 91/07172 | A1 | 5/1991 |
| WO | 93/11773 | A1 | 6/1993 |
| WO | 94/22899 | A1 | 10/1994 |
| WO | 98/09982 | A1 | 3/1998 |
| WO | 98/16228 | A1 | 4/1998 |
| WO | 98/21175 | A1 | 5/1998 |
| WO | 98/52542 | A1 | 11/1998 |
| WO | 99/17754 | A1 | 4/1999 |
| WO | 99/25359 | A1 | 5/1999 |
| WO | 99/53926 | A1 | 10/1999 |
| WO | 00/07567 | A1 | 2/2000 |
| WO | 00/17200 | A1 | 3/2000 |
| WO | 00/21487 | A1 | 4/2000 |
| WO | 00/28979 | A1 | 5/2000 |
| WO | 01/22955 | A2 | 4/2001 |
| WO | 01/28563 | A1 | 4/2001 |
| WO | 01/56573 | A1 | 8/2001 |
| WO | 01/78738 | A1 | 10/2001 |
| WO | 01/89491 | A1 | 11/2001 |
| WO | 01/98174 | A1 | 12/2001 |
| WO | 01/98175 | A1 | 12/2001 |
| WO | 02/28368 | A1 | 4/2002 |
| WO | 02/062317 | A2 | 8/2002 |
| WO | 02/083113 | A2 | 10/2002 |
| WO | 02/091866 | A1 | 11/2002 |
| WO | 03/006310 | A1 | 1/2003 |
| WO | 03/043905 | A2 | 5/2003 |
| WO | 03/086349 | A1 | 10/2003 |
| WO | 2004/103379 | A1 | 12/2004 |
| WO | 2004/105727 | A2 | 12/2004 |
| WO | 2004/110460 | A1 | 12/2004 |
| WO | 2005/004853 | A1 | 1/2005 |

OTHER PUBLICATIONS

Braga, et al., "Making crystals from crystals: a green route to crystal engineering and polymorphism", Chem. Commun., pp. 3635-3645, (2005).

Gracia-Marcos, et al., "Inhaled corticosteroids plus long-acting β2-agonists as a combined therapy in asthma", Expert Opin. Pharmacother., vol. 4, No. 1, pp. 23-39, (2003).

STN registry for Glycopyrronium, 2 pages, 2004.

STN registry for Ciclesonide, 1 page, 1990.

Gilbert, "Chapter 7: Enzyme Mechanism", Basic Concept in Biochemistry, 2nd ed., e-book, (2000).

Belvisi, et al., "Soft steroids: a new approach to the treatment of inflammatory airways diseases", Pulmonary Pharmacology & Therapeutics, vol. 16, pp. 321-325, (2003).

Armarego, et al., Purification of Laboratory Chemicals, 4th Ed., Elsevier, pp. 28-29, (1996).

Wetscher, et al., "Respiratory Symptoms in Patients with Gastroesophageal Reflux Disease following Medical Therapy and following Antireflux Surgery", The American Journal of Surgery, vol. 174, No. 6, pp. 639-643, (1997).

Simon, et al., "Soraprazan: Setting New Standards in Inhibition of Gastric Acid Secretion", The Journal of Pharmacology and Experimental Therapeutics, vol. 321, No. 3, pp. 866-874, (2007).

The Merck Index, 12 ed., (1996), The Merck Manual indicates that the boiling point of Acetone is 56.5° C. (p. 12, Entry 64), and the boiling point of ethanol is 78° C. (p. 641, Entry 3806).

West, et al., Solid Solutions, Solid State Chemistry and its Applications, pp. 358 and 365, (1988).

Vippagunta, et al., Advanced Drug Delivery Reviews, 2001, vol. 48, pp. 3-26.

Taylor, et al., "A dose-dependent effect of the novel inhaled corticosteroid ciclesonide on airway responsiveness to adenosine-5'-monophosphate in asthmatic patients", Am. J. Respir. Crit. Care Med., vol. 160, pp. 237-243, (1999).

Postma, et al., "Treatment of asthma by the inhaled corticosteroid ciclesonide given either in the morning or evening", Eur. Respir. J., vol. 17, pp. 1083-1088, (2001).

Maessen, et al., "Effects of formoterol in apparently poorly reversible chronic obstructive pulmonary disease", Eur. Respir. J., vol. 13, pp. 1103-1108, (1999).

Akpinarli, et al., "Effect of formoterol on clinical parameters and lung functions in patients with bronchial asthma: a randomised controlled trial", Arch. Dis. Child., vol. 81, pp. 45-48, (1999).

* cited by examiner

COMBINATION MEDICAMENT

This application is a continuation application of U.S. Ser. No. 10/537,356, filed Jun. 3, 2005, which is a national phase application under 35 USC §371 of PCT/EP2003/014045, filed Dec. 11, 2003.

FIELD OF APPLICATION OF THE INVENTION

The invention relates to a novel combination preparation for the therapy of airway diseases.

KNOWN TECHNICAL BACKGROUND

Various novel glucocorticoids are disclosed, inter alia also the active compound ciclesonide, in DE-A 41 29 535. The combination of selected glucocorticoids with specific $\beta_2$-sympathomimetics is described in various patent applications (e.g. EP 0 416 950, EP 0 416 951, WO93/11773 or DE-A 19541689). WO01/89492 relates to a stable powder formulation comprising formoterol, a glucocorticosteroid and a carrier or diluent for use in the treatment of respiratory diseases.

DESCRIPTION OF THE INVENTION

It was the object of the present invention to make available an antiasthmatic to be administered locally, which fulfils the following conditions:
good local (topical) action
lack of systemic (side) effects
low oral bioavailability
rapid resolution of bronchospasm
good antiinflammatory action
good suitability for long-term therapy
favourable influence on bronchial hyperreactivity.

It has now been found that the combined use of the active compound ciclesonide with the $\beta_2$-sympathomimetic R,R-formoterol fulfils the abovementioned conditions in an outstanding manner.

The invention thus relates to the combined use of ciclesonide with R,R-formoterol in the treatment of airway diseases.

Ciclesonide is the INN for an active compound having the chemical name [11β,16α-(R)]-16,17-[(cyclohexylmethylene)bis(oxy)]-11-hydroxy-21-(2-methyl-1-oxopropoxy)pregna-1,4-diene-3,20-dione. Ciclesonide and its preparation are described in DE-A 4129535. According to the invention, the name ciclesonide also includes solvates of ciclesonide, physiologically functional derivatives of ciclesonide or solvates thereof. Physiologically functional derivatives of ciclesonide, which can be mentioned in connection with the present invention, are preferably chemical derivatives of ciclesonide which have a similar physiological function to ciclesonide, for example the 21-hydroxy derivative of ciclesonide. The 21-hydroxy compound has the chemical name 16α,17-(22R,S)-cyclohexylmethylenedioxy-11β,21-dihydroxy-pregna-1,4-diene-3,20-dione. This compound and its preparation are disclosed in WO 94/22899. According to the invention, the name "ciclesonide" is understood as meaning not only the pure R epimer of the compound [11β,16α] 16,17-[(cyclohexylmethylene)bis(oxy)]-11-hydroxy-21-(2-methyl-1-oxopropoxy)pregna-1,4-di-ene-3,20-dione but also R/S epimer mixtures in any desired mixing ratio (that is the compounds [11β,16α(R)]16,17-[(cyclohexylmethylene)bis(oxy)]-11-hydroxy-21-(2-methyl-1-oxopropoxy)pregna-1,4-diene-3,20-dione and [11β,16α(S)]-16,17-[(cyclohexylmethylene)bis(oxy)]-11-hydroxy-21-(2-methyl-1-oxopropoxy)pregna-1,4-diene-3,20-dione), those being preferred which essentially consist of R epimers. According to the invention, essentially consisting of R epimers means that the proportion of S epimers in the mixture is less than or equal to 5%, preferably less than or equal to 1%.

Formoterol is the chemical compound N-[2-hydroxy-5-(1-hydroxy-2-((2-(4-methoxyphenyl)-1-methyl-ethyl)amino) ethyl)phenyl]formamide. Formoterol can exist in the form of various stereoisomers. The combinations according to the invention are preferably the combination of ciclesonide with R,R-formoterol. According to the invention, the active compound name R,R-formoterol can also include mixtures of various stereoisomers of formoterol. Preferably, such mixtures essentially consist of R,R-formoterol. According to the invention, consisting essentially of R,R-formoterol means that the proportion of R,R-formoterol in the mixture of the stereoisomers of formoterol is greater than or equal to 95%, preferably greater than or equal to 99%. Stereoisomers of formoterol are described, for example, in WO98/21175, WO99/17754, U.S. Pat. Nos. 6,068,833 and 5,795,564. U.S. Pat. Nos. 6,268,533, 6,472,563 and WO 00/21487 are related to a specific salt of R,R-Formoterol, the L-tartrate salt of formoterol. WO01/89491 is related to a novel micronisation process for manufacturing a stable formulation for formoterol and a carrier/diluent comprising a carbohydrate such as a lactose. WO98/31351 is related to a dry powder composition comprising formoterol and a carrier substance, wherein the formulation has a poured bulk density of from 0.28 to 0.38 g/ml. WO01/39745 is related to a dry powder composition comprising formoterol and a pharmaceutically acceptable particulate diluent or carrier in an amount of 400 μg to 5000 μg per μg of formoterol.

R,R-Formoterol can be present as such or in chemically bonded form. It is understood by this that R,R-formoterol can also be present in the form of pharmacologically tolerable salts and/or as solvates (e.g. hydrates) etc. Suitable pharmacologically tolerable salts here are in particular water-soluble and water-insoluble acid addition salts with acids such as hydrochloric acid, hydrobromic acid, phosphoric acid, nitric acid, sulphuric acid, acetic acid, citric acid, D-gluconic acid, benzoic acid, 2-(4-hydroxybenzoyl) benzoic acid, butyric acid, sulphosalicylic acid, maleic acid, lauric acid, malic acid, fumaric acid, succinic acid, oxalic acid, tartaric acid, embonic acid, stearic acid, toluenesulphonic, methanesulphonic acid, or 1-hydroxy-2-naphthoic acid, it being possible for the acids to be employed in the salt preparation—depending on whether it is a mono- or polybasic acid and depending on which salt is desired—in an equimolar quantitative ratio or one differing therefrom. In an embodiment of the invention R,R-formoterol is present in the medicament according to the invention as salt with an acid selected from the group of hydrochloric acid, hydrobromic acid, phosphoric acid, nitric acid, sulphuric acid, acetic acid, citric acid, D-gluconic acid, benzoic acid, 2-(4-hydroxybenzoyl) benzoic acid, butyric acid, sulphosalicylic acid, maleic acid, lauric acid, malic acid, fumaric acid, succinic acid, oxalic acid, tartaric acid, embonic acid, stearic acid, toluenesulphonic, methanesulphonic acid and 1-hydroxy-2-naphthoic acid.

Preferably, the fumarate of R,R-formoterol may be mentioned, particularly preferably in the form of the dihydrate.

Airway diseases which may be mentioned are in particular allergen- and inflammatorily-induced bronchial diseases [bronchitis, obstructive bronchitis (in particular COPD=chronic obstructive pulmonary disease), spastic bronchitis, allergic bronchitis, allergic asthma, bronchial asthma], which can be treated by the combination according to the invention also in the sense of a long-term therapy (if desired with respective adjustment of the dose of the individual components to the present conditions, for example the conditions subject to variations related to the time of year).

Within the meaning of the present invention, "use" is primarily understood as meaning topical application in inhalative form. For this, the active compounds are preferably administered inhalatively in the form of aerosols, the aerosol particles preferably having a diameter of 0.5 to 10 µm, advantageously of 2 to 6 µm. The aerosol can be generated in the manner known to the person skilled in the art, e.g. by propellant-free use of micronized active compounds from inhalation capsules.

Combined use within the meaning of the present invention can be understood as meaning that the substances are simultaneously administered inhalatively from an apparatus suitable for this. Preferred apparatuses, which may be mentioned here are powder inhalers (dry aerosol generators). In this context, the substances can be present already mixed, or they can be taken out simultaneously from separate pack units during inhalation.

The use of two separate pack units offers the advantage that the dose of ciclesonide to be administered on the one hand and of R,R-formoterol on the other hand can be matched with one another and can be exactly suited to the individual case.

Combined use is in the sense of the present invention, however, can also be understood as meaning that the administration of the individual components takes place directly one after the other or else also with a relatively large time interval, advantageously the R,R-formoterol first being administered inhalatively in order to relax the airways for the subsequent administration of the ciclesonide in order to ensure a higher and more uniform deposition of the ciclesonide in the airways and in the lung.

According to the invention, combined use or combination in particular also means that the active compounds ciclesonide and R,R-formoterol act in a synergistic manner (i.e. superadditive manner).

The active compounds are administered in an order of magnitude customary for the individual dose, it being possible on account of the mutually positively influencing and reinforcing individual actions to lower the respective doses in the combined administration of the active compounds compared with the norm. Customarily, the ciclesonide is administered, if desired in the form of a single, double or triple dose per day, in a dose of 0.05 to 1 mg per day. The R,R-formoterol is administered in a dose of 10 to 50 µg per day by means of a single, double or triple dose per day.

The present invention is further related to a method of treatment of an airway disease in a patient comprising administration of a therapeutically effective amount of a medicament according to the present invention to the patient in need thereof by means of a dry powder inhaler. Preferably the airway disease is a allergen- and inflammatorily-induced bronchial disease such as bronchitis, obstructive bronchitis, COPD (chronic obstructive pulmonary disease), spastic bronchitis, allergic bronchitis, allergic asthma and bronchial asthma.

In a preferred embodiment ciclesonide is administered in a dose of 0.05 to 1 mg per day and R,R-formoterol is administered in a dose of 10 to 50 µg per day in the method of treatment according to the present invention. In a particularly preferred embodiment the method of treatment according to the present invention is a once daily administration regimen.

In addition to the active compounds, the administration forms according to the invention if desired additionally contain the excipients and or vehicles necessary or optionally further active compounds. According to the invention, these are those excipients and or vehicles which are needed for administration forms which are administered by means of powder inhalers. By way of example, fillers such as, for example, lactose in powder inhalers may be mentioned here.

For the purposes of inhalation, in the case of powder inhalers a number of technical solutions are available (e.g. Diskhaler®, Rotadisk®, Turbohaler® or the inhaler systems described in European patent applications EP 0 505 321, EP 407028, EP 650410, EP 691865 or EP 725725), using which an optimum administration of active compound is achievable.

EXAMPLE

Inhalation Capsule

In a Turbula mixer, 400 mg of micronized ciclesonide, 119 mg of micronized formoterol fumarate dihydrate (=93 mg formoterol) and 36.1 g of lactose monohydrate Ph. Eur. II are mixed in two portions. The mixture screened through a 0.71 mm screen is transferred to the mixing container of a planetary mixer. After admixing a further 63.0 g of lactose monohydrate Ph. Eur. II, 25 mg of the powder mixture are filled into capsules of size 3, which can be administered using a commercially available powder inhaler. One puff of spray contains 100 µg of ciclesonide and 24 µg of R,R-formoterol.

Multidose Powder Inhaler 1000 g of lactose monohydrate (Ph. Eur. 4) are added through a screen mill. In a Turbula mixer, 300 mg of micronized R,R-formoterol fumarate dihydrate, screened through a 0.5 mm screen, and 97.2 g of the deagglomerated lactose monohydrate are mixed. 250 g of the deagglomerated lactose monohydrate are filled into a stirrer/mixer and mixed with 2.5 g of ciclesonide micronized screened through a 0.5 mm screen. The formoterol-lactose premixture is added through a 0.5 mm screen to the mixing container of the stirrer/mixer and briefly intermixed. After admixing a further 650 g of deagglomerated lactose monohydrate, 1.5 g of the powder mixture are filled into the powder reservoir of a multidose powder inhaler using a suitable filling machine. After closing the reservoir chamber with a stopper, the attachment of the mouthpiece and/or the protective cap, the powder inhaler is sealed into a suitable protective film for protection from atmospheric moisture. A powder inhaler contains at least 60 individual doses (20.0 mg of powder) for each 50 µg of ciclesonide and 6 µg of R,R-formoterol fumarate dihydrate.

Multidose Powder Inhaler 60 mg of micronized formoterol fumarate dihydrate and 7.27 g of lactose monohydrate Ph. Eur. 4 are screened through a 0.5 mm screen and mixed in the Turbula mixer. The formoterol-lactose premixture is again screened through a 0.5 mm screen and added with 2.67 g of the screened micronized ciclesonide and 90 g of screened lactose monohydrate Ph. Eur. 4 to a stainless steel vessel and mixed in the Turbula mixer. 1.2 g of the powder mixture are filled into the powder reservoir of a multidose powder inhaler using a suitable filling machine. After closing the reservoir chamber with a stopper, the attachment of the mouthpiece and/or the protective cap, the powder inhaler is sealed into a suitable protective film for protection from atmospheric moisture.

A powder inhaler contains at least 120 individual doses (7.5 mg of powder) for each 200 µg of ciclesonide and 4.5 µg of R,R-formoterol fumarate dihydrate.

The invention claimed is:

1. A pharmaceutical composition comprising as the sole active compounds a combination of the active compound ciclesonide or an epimer thereof and the active compound R,R-formoterol or a salt thereof, and optionally comprising excipients and/or vehicles.

2. The pharmaceutical composition according to claim 1, wherein the active compound ciclesonide is present as its R epimer in an amount greater than 95%.

3. The pharmaceutical composition according to claim 1, wherein the active compound ciclesonide is present as its R epimer in an amount greater than 95%, and the active compound R,R-formoterol is present as a salt.

4. The pharmaceutical composition according to claim 3, wherein the active compound R,R-formoterol is present as a salt with an acid selected from the group consisting of hydrochloric acid, hydrobromic acid, phosphoric acid, nitric acid, sulphuric acid, acetic acid, citric acid, D-gluconic acid, benzoic acid, 2-(4-hydroxybenzoyl) benzoic acid, butyric acid, sulphosalicylic acid, maleic acid, lauric acid, malic acid, fumaric acid, succinic acid, oxalic acid, tartaric acid, embonic acid, stearic acid, toluenesulphonic, methanesulphonic acid and 1-hydroxy-2-naphthoic acid.

5. The pharmaceutical composition according to claim 4, wherein the acid is fumaric acid or tartaric acid.

6. A method of treating an airway disease in a patient comprising administering to a patient in need thereof the pharmaceutical composition according to claim 1 in an administration form suitable for inhalative administration by means of a powder inhaler, wherein the combination is a fixed combination.

7. The method according to claim 6, wherein the active compound ciclesonide is present as its R epimer in an amount greater than 95%.

8. A method of treating an airway disease in a patient comprising administering to a patient in need thereof a therapeutically effective amount of the pharmaceutical composition according to claim 1 by means of a dry powder inhaler.

9. The method according to claim 8, wherein the airway disease is selected from the group consisting of bronchitis, obstructive bronchitis, COPD (chronic obstructive pulmonary disease), spastic bronchitis, allergic bronchitis, allergic asthma and bronchial asthma.

10. The method according to claim 8, wherein ciclesonide or an epimer thereof is administered in a dose of 0.05 to 1 mg per day and R,R-formoterol or a salt thereof is administered in a dose of 10 to 50 µg per day.

11. The method according to claim 10, wherein the dose is administered once daily.

12. The pharmaceutical composition according to claim 1, further comprising an excipient and/or vehicle.

13. The pharmaceutical composition according to claim 12, wherein the excipient and/or vehicle is lactose.

14. The pharmaceutical composition according to claim 12, wherein the excipient and/or vehicle is lactose monohydrate.

15. The method according to claim 6, wherein the pharmaceutical composition further comprises an excipient and/or vehicle.

16. The method according to claim 15, wherein the excipient and/or vehicle is lactose.

17. The method according to claim 15, wherein the excipient and/or vehicle is lactose monohydrate.

18. The pharmaceutical composition according to claim 1, wherein the active compounds are administered inhalatively in the form of aerosol particles having a diameter of 0.5 to 10 µm.

19. The pharmaceutical composition according to claim 1, wherein the active compounds are administered inhalatively in the form of aerosol particles having a diameter of 2 to 6 µm.

\* \* \* \* \*